US 9,259,596 B2

(12) United States Patent
Jager (10) Patent No.: US 9,259,596 B2
(45) Date of Patent: *Feb. 16, 2016

(54) MOBILE X-RAY UNIT
(71) Applicant: NUCLETRON OPERATIONS B.V., Veenendaal (NL)
(72) Inventor: Wim de Jager, Rhenen (NL)
(73) Assignee: NUCLETRON OPERATIONS, B.V., Veenendaal (NL)
( * ) Notice: Subject to any disclaimer, the term of this patent is extended or adjusted under 35 U.S.C. 154(b) by 0 days.

This patent is subject to a terminal disclaimer.

(21) Appl. No.: 14/697,761
(22) Filed: Apr. 28, 2015
(65) Prior Publication Data
US 2015/0224344 A1    Aug. 13, 2015

Related U.S. Application Data (63) Continuation of application No. 13/335,863, filed on Dec. 22, 2011, now Pat. No. 9,036,787.
(60) Provisional application No. 61/426,933, filed on Dec. 23, 2010.

(30) Foreign Application Priority Data

Dec. 22, 2010    (NL) ...................................... 2005900

(51) Int. Cl.
*A61N 5/10*    (2006.01)
(52) U.S. Cl.
CPC ................ *A61N 5/1049* (2013.01); *A61N 5/10* (2013.01); *A61N 2005/1056* (2013.01); *A61N 2005/1091* (2013.01)
(58) Field of Classification Search
CPC ............. A61B 6/06; A61B 6/08; A61B 6/44; H05G 1/00; H05G 1/02; H05G 1/04; A61N 5/10; A61N 5/1077; A61N 5/1083; A61N 5/1092; A61N 5/1094; A61N 5/0643; A61N 5/065; A61N 5/0654; A61N 5/0655; A61N 5/0664; A61N 5/0665; A61N 5/0666; H01J 5/00; H01J 5/02; H01J 5/18; H01J 35/00; H01J 35/02; H01J 35/16; H01J 35/18; H01J 35/32; G21K 1/00; G21K 1/02; G21F 5/00; G21F 5/02; G21F 5/04; G21F 5/06
USPC ........ 378/51, 56, 64, 65, 68, 91, 95–98, 98.3, 378/98.5, 98.8, 119, 121, 140, 162–166, 378/193, 204–206, 210; 250/370.01, 250/370.06, 370.07, 370.08, 370.09, 371, 250/393, 395, 493.1, 496.1, 503.1, 522.1, 250/526
See application file for complete search history.

(56) References Cited

U.S. PATENT DOCUMENTS 3,767,931 A    10/1973    Williams
5,031,203 A    7/1991    Trecha
(Continued)

FOREIGN PATENT DOCUMENTS

WO    WO 2008/118198    10/2008

OTHER PUBLICATIONS

Search Report and Written Opinion in related Netherlands Application No. 2005900, dated May 28, 2011 (8 pages).
(Continued)

*Primary Examiner* — Anastasia Midkiff
(74) *Attorney, Agent, or Firm* — Finnegan, Henderson, Farabow, Garrett & Dunner, LLP (57) ABSTRACT

One embodiment of the present disclosure is directed to a mobile X-ray unit. The mobile X-ray unit may include a base and an arm associated with the base. The arm may be configured to support an X-ray applicator having an X-ray tube. The X-ray tube may be configured to generate an X-ray beam. The X-ray applicator may include an exit surface through which the X-ray beam passes in use. The X-ray unit may further include an applicator cap for covering at least the exit surface of the X-ray applicator.

17 Claims, 9 Drawing Sheets

(56) References Cited

U.S. PATENT DOCUMENTS

| | | | |
|---|---|---|---|
| 5,090,043 A | 2/1992 | Parker et al. | |
| 5,708,696 A | 1/1998 | Kantor | |
| 6,267,502 B1 | 7/2001 | McNeirney et al. | |
| 6,302,581 B1 | 10/2001 | Sliski et al. | |
| 6,702,459 B2 | 3/2004 | Barnes et al. | |
| 8,050,384 B2 | 11/2011 | Carol et al. | |
| 8,520,801 B2 | 8/2013 | Henning | |
| 9,036,787 B2 * | 5/2015 | de Jager | 378/140 |
| 2003/0048875 A1 | 3/2003 | Mihara et al. | |
| 2007/0076851 A1 | 4/2007 | Pellegrino | |
| 2009/0190722 A1 | 7/2009 | Windt | |
| 2010/0246766 A1 | 9/2010 | Kindlein et al. | |
| 2010/0280374 A1 | 11/2010 | Roberts et al. | |

OTHER PUBLICATIONS

Topex, Inc., "SRT 100 Superficial Radiotherapy System for the Treatment of Skin Cancer," http://www.harpell.ca/wp-content/uploads/2009/11/topexbrochure_v10.pdf, (6 pages).

Topex, Inc., "Regulatory Information," http://www.tpoexmedical.com/product2.html, 2007 (1 page).

* cited by examiner

MOBILE X-RAY UNIT

CROSS-REFERENCE TO RELATED APPLICATIONS

This is a continuation of application Ser. No. 13/335,863, filed Dec. 22, 2011, which claims the benefit of priority based on U.S. Provisional Patent Application No. 61/426,933, filed Dec. 23, 2010, and Netherlands Patent Application No. 2005900, filed Dec. 22, 2010, which are ail incorporated herein by reference.

FIELD OF THE INVENTION

The present disclosure relates generally to a mobile X-ray unit. The present disclosure also relates a method of manufacturing the mobile X-ray unit.

BACKGROUND OF THE INVENTION

The incidence rate of skin cancer has substantially increased in the last decade of the $20^{th}$ century. It is appreciated that over 1.3 million new skin cancers are diagnosed annually, which is increasing at a rate of about 5% per year. Increased exposure to the sun without skin protection and a decreased ozone layer are regarded as the main causes of this increase—a problem estimated to be costing over 1 billion Euros in annual medical treatment expenses. Over 80% of skin cancers occur in the head and neck regions with 50% occurring in patients over 60 years of age. It is expected that a portion of the senior population will double in year 2025 compared to the present demographics. Because of the growing incidence of skin cancer and increasing share of the senior population in the overall demographics, much focus has been placed on cancer treatments and cancer treatment logistics.

Non-proliferative cancers, which are defined by substantially superficial lesions, may be treated in different ways. In one example, non-proliferative cancers may be treated surgically. Surgery may have certain drawbacks, such as, for example, long waiting lists, complications related to post-treatment care, and risk of infection. In another example, patients may undergo irradiation using electrons of soft X-rays. Irradiation may have an advantage of being non-invasive and of a short duration (a treatment session may be as short as 2 to 4 minutes). It will be appreciated that usually the integral treatments using radiotherapeutic techniques may require a number of sessions.

Recently, the use of a mobile and portable X-ray unit has been suggested, which may be used inside a hospital radiotherapy department. An embodiment of such portable unit is described in US 2007/0076851. Such units include an X-ray source and a filtering device having a plurality of filters rotatably arranged with respect to a focal point of the X-ray tube for changing filtering characteristics on demand. The plurality of filters are arranged in a filtering device, which is transversely arranged with respect to a longitudinal axis of the X-ray tube. These units, while effective, have certain drawbacks. For example, existing X-ray units may require a considerable time for sterilization and time for meeting other hygienic requirements set forth for equipment used in medical treatment.

SUMMARY OF THE INVENTION

It is an object of the disclosure to provide a mobile X-ray unit having improved operational characteristics in particular, with regard to hygienic requirements. To this end, in accordance with an embodiment of the present disclosure, an applicator cap may be provided on an X-ray applicator associated with the mobile X-ray unit. The applicator cap may cover at least an exit surface of the X-ray applicator.

It will be appreciated that the terms 'mobile' and 'portable' in the context of the present application may be interchanged as these terms equally relate to an easily moved or transported device, for example, a device which may be moved or transported by a single individual.

It may be advantageous to provide an applicator cap on an X-ray applicator associated with an X-ray unit, which may have many functions in use. In one example, the applicator cap may be used for protecting the exit surface of the X-ray applicator from intra-patient contamination. In another example, the thickness of the applicator cap in a direction of X-ray beam propagation may be sufficient for substantially eliminating electron contamination from the X-ray beam. Those skilled in the art will readily appreciate the relationship between the energy of the secondary electrons emanating from the X-ray tube and a required thickness of a given material, such as, for example plastic, glass, ceramics, sufficient to fully intercept these electrons. In yet another example, the applicator cap may function as a heat absorber to dissipate the elevated temperature of the X-ray applicator. As a result the patient will feel the applicator contacting the skin as a slightly warm object.

In some embodiments, the applicator cap may be manufactured from PVDF (polyvinyldienefluoride) and may have a thickness of about 0.4-0.7 mm, and preferably 0.6 mm, across the window portion. The applicator cap may have a density of about 1.75-1.8, and preferably 1.78. Alternatively, the applicator cap may have a thickness of about 0.3-0.6 mm, and preferably 0.5 mm, across the window portion. In this embodiment, the applicator cap may have a density of 1.30-1.45, and preferably 1.39, and may be manufactured from PPSU (polyphenylsulphone). It is found that these materials may be particularly suitable as they as stable under influence of the X-rays and are suitable for different types of sterilization procedures, such as chemical sterilization, or sterilization under elevated temperatures.

In various embodiments, the X-ray applicator may include a light source arranged for delineating the X-ray beam. The applicator cap may be at least 50% transparent to the wavelength of light generated by the light source. In some embodiments, the applicator cap is disposable after a single use of the X-ray applicator.

In various embodiments of the present disclosure, a distance between an X-ray target and a collimator is in the range between 4 and 10 cm, and preferably between 5 and 6 cm.

It may found that by setting a distance between the X-ray target and the collimator in the range between 4 and 10 cm, and preferably to a distance of about 5 to 6 cm improved beam characteristics may be achieved. For example, it is found that improved beam flatness as well as sharpened penumbra are achievable for the target-collimator distance between 4 and 10 cm, and particularly for the target-collimator distance between 5 and 6 cm. For example, for the target-collimator distance of about 5 cm penumbra of 1.5-1.8 mm is achievable (specified for 20/80% lines).

It is appreciated that such sharpened penumbra is important particularly for treating of small lesions, like skin cancers, so as to minimize treatment of healthy tissue.

In various embodiments of the present disclosure, the target and the collimator may be received in a substantially cylindrically shaped X-ray tube having a longitudinal axis. A direction of propagation of the X-ray beam may be substantially parallel to the longitudinal axis of the X-ray tube.

The anode-collimator geometry may be advantageous. In particular, the axis of the X-ray tube may substantially coincide with a direction of propagation of the generated X-ray beam. This arrangement may permit the x-ray tube and an x-ray applicator to have the same longitudinal axis. It will be appreciated that the X-ray tube, accommodated in the X-ray applicator, represents a relatively slim (outer diameter of less than 10 cm) elongated cylinder (length of about 30 cm), which is preferably displaced in a vertical direction for delivering the X-ray beam to the patient. Once the internal geometry of the X-ray tube is co-axial, the weight of the X-ray tube may be suitably balanced enabling easy and reproducible displacement of the articulated arm supporting the X-ray applicator.

Another embodiment of the present disclosure is directed to a method for manufacturing a mobile X-ray unit. The mobile X-ray unit may include a base for accommodating at least a control unit, a power supply, and a cooler. The mobile X-ray unit may further include an articulated arm supporting an X-ray applicator having an X-ray tube. The method may include providing an applicator cap on or near the exit surface of the X-ray applicator. In some embodiments, the method may further include arranging the X-ray tube with a target for generating an X-ray beam and a collimator for shaping the generated X-ray beam; and setting a distance between the target and the collimator in the range between 4 and 10 cm.

Another embodiment of the present disclosure relates to an applicator cap for an X-ray unit including an X-ray tube accommodated in an X-ray applicator having an exit surface. The applicator cap may be arranged to covering at least the exit surface.

In some embodiments, the applicator cap may be disposable. Further, a thickness of the cap in a direction of the beam propagation is sufficient for substantially eliminating electron contamination from the X-ray beam. An applicator cap may be advantageously manufactured from a substantially transparent material so as to enable visualization of delineation between the exit surface of the X-ray applicator and a lesion conceived to be treated.

These and other aspects of the invention will be discussed with reference to drawings wherein like reference numerals or signs relate to like elements. It will be appreciated that the drawings are presented for illustration purposes only and may not be used for limiting the scope of the appended claims.

BRIEF DESCRIPTION OF THE DRAWINGS

FIG. 6, E-E presents a cross-section along line VII-E of the X-ray tube of FIG. 6, according to embodiments of the present disclosure.

FIG. 6, F-F presents a cross-section along line VII-F of the X-ray tube of FIG. 6, according to embodiments of the present disclosure.

DETAILED DESCRIPTION OF THE DRAWINGS

Figure 1A:
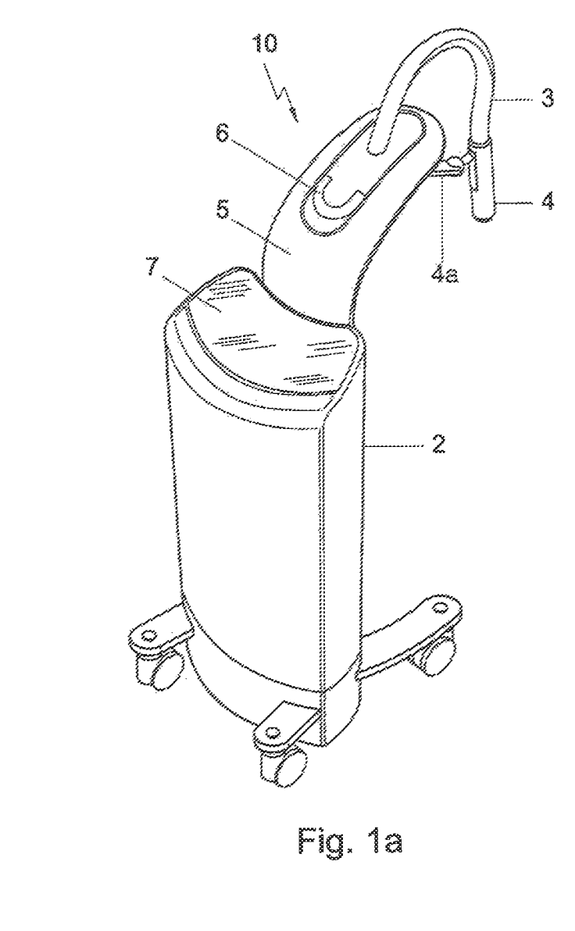
FIG. 1a presents a perspective view of a mobile X-ray unit, according to embodiments of the present disclosure.
Figure 3:
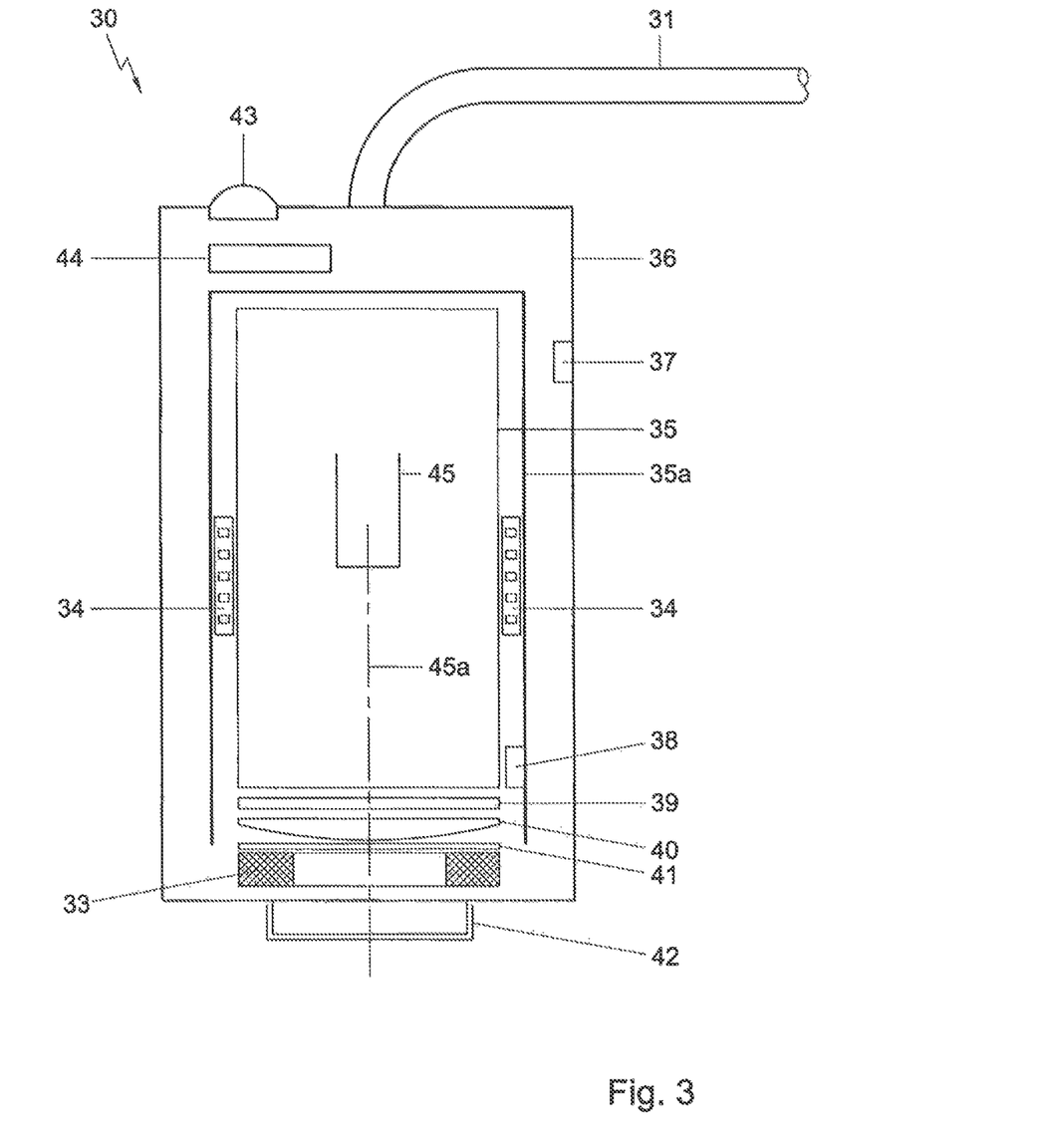
FIG. 3 presents a cross-sectional view of the X-ray applicator of the mobile X-ray unit, according to embodiments of the present disclosure.

FIG. 1a presents a schematic view of a mobile X-ray unit according to an exemplary embodiment of the present disclosure. The mobile X-ray unit 10 may have a base 2 including at least a power supply unit, a cooling system, and a control unit for controlling an operation of an X-ray applicator 4. The X-ray applicator 4 may include an X-ray tube (FIG. 3) disposed in an outer housing (FIG. 3). The X-ray applicator 4 may be connected to the base 2 via flexible cables 3, which may be at least partially received in a displaceable panel 5. The X-ray applicator 4 may be supported by an articulated arm 4a, which may include a pivot for altering the position and/or angle of the X-ray applicator 4 in space. The articulated arm 4a may be connected to the displaceable panel 5 to permit a vertical position of the X-ray applicator 4. Preferably, the displaceable panel 5 is provided with a handle 6 enabling easy manipulation thereof. The displaceable panel 5 may be guided along suitable rails for enabling a substantially smooth and shock-free displacement thereof.

The displaceable panel 5 may also be referred to as a displaceable mast. It may be advantageous to allow the mast to be displaceable along a substantially upright axis with respect to the base 2. It will be appreciated that the substantially upright axis extends in a substantially vertical direction, which is generally upright. However, it will be further appreciated that the terms 'generally upright' or 'substantially vertical' may relate to a direction substantially perpendicular (+−20 degrees) to a plane of the surface on which the mobile X-ray unit is sitting.

Figure 1B:
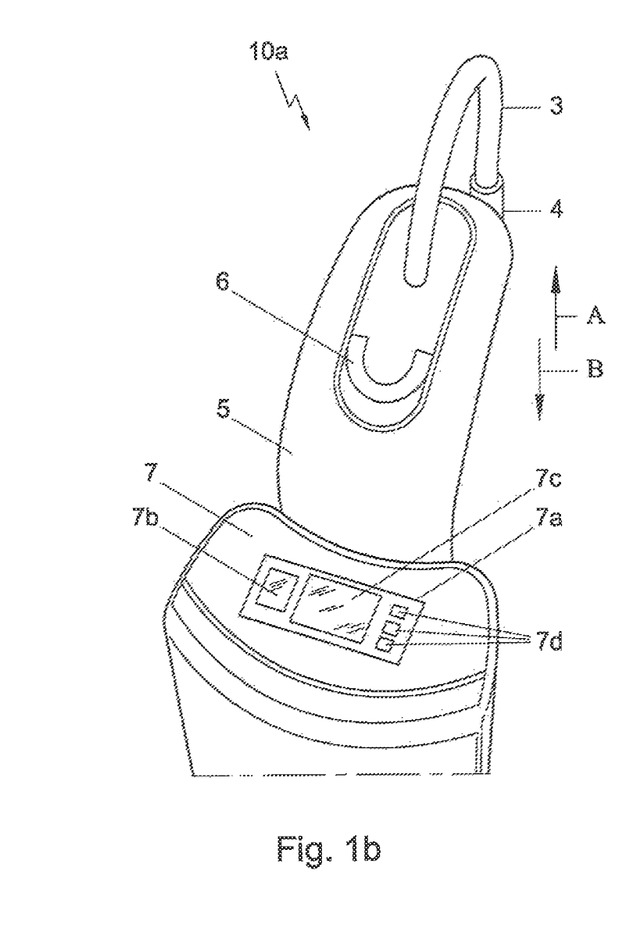
FIG. 1b presents a partial perspective view of a displaceable panel of the mobile X-ray unit illustrated in FIG. 1a, according to embodiments of the present disclosure.

FIG. 1b presents a schematic view of an embodiment of a displaceable panel 5 of the mobile X-ray unit 10. In this enlarged view 10a specific elements of the displaceable panel 5 are depicted. Accordingly, a handle 6 may be implemented as a mechanical item for pulling or pushing the panel 5. Alternatively, the handle 6 may be arranged as an electrical actuator for triggering motors (not shown) for displacing the displaceable panel 5. For example, when the handle 6 is pulled the motors may be activated for causing the displaceable panel 5 to displace in a direction A. Pushing of the handle 6 may cause lowering of the displaceable panel 5 in a direction B opposite direction A. In some embodiments, the mobile X-ray unit 10 includes stops, limits, or other known structures for limiting the movement of the displaceable panel 5. This may ensure mechanical stability of the system on one hand (limitation of the upper level) and, on the other hand, may be beneficial for preventing cable damage (limitation of the lower level). It is contemplated that the displaceable panel 5 may be movable using built-in rails whose length may be chosen for limiting the displacement range of the panel 5 in a desirable way.

The base 2 may further include a display 7, which may function as a suitable user interface 7a. For example, the patient data, such as a photo of the patient and/or a photo of a lesion may be provided in window 7b, whereby relevant patient information, such as the date of birth, gender, dose prescription and dose delivery protocol and other patient information may be displayed in window 7c. Buttons 7d may be provided as touch functionality to input data. Additionally and/or alternatively, suitable hardware switches or buttons may be provided as well.

Figure 1C:
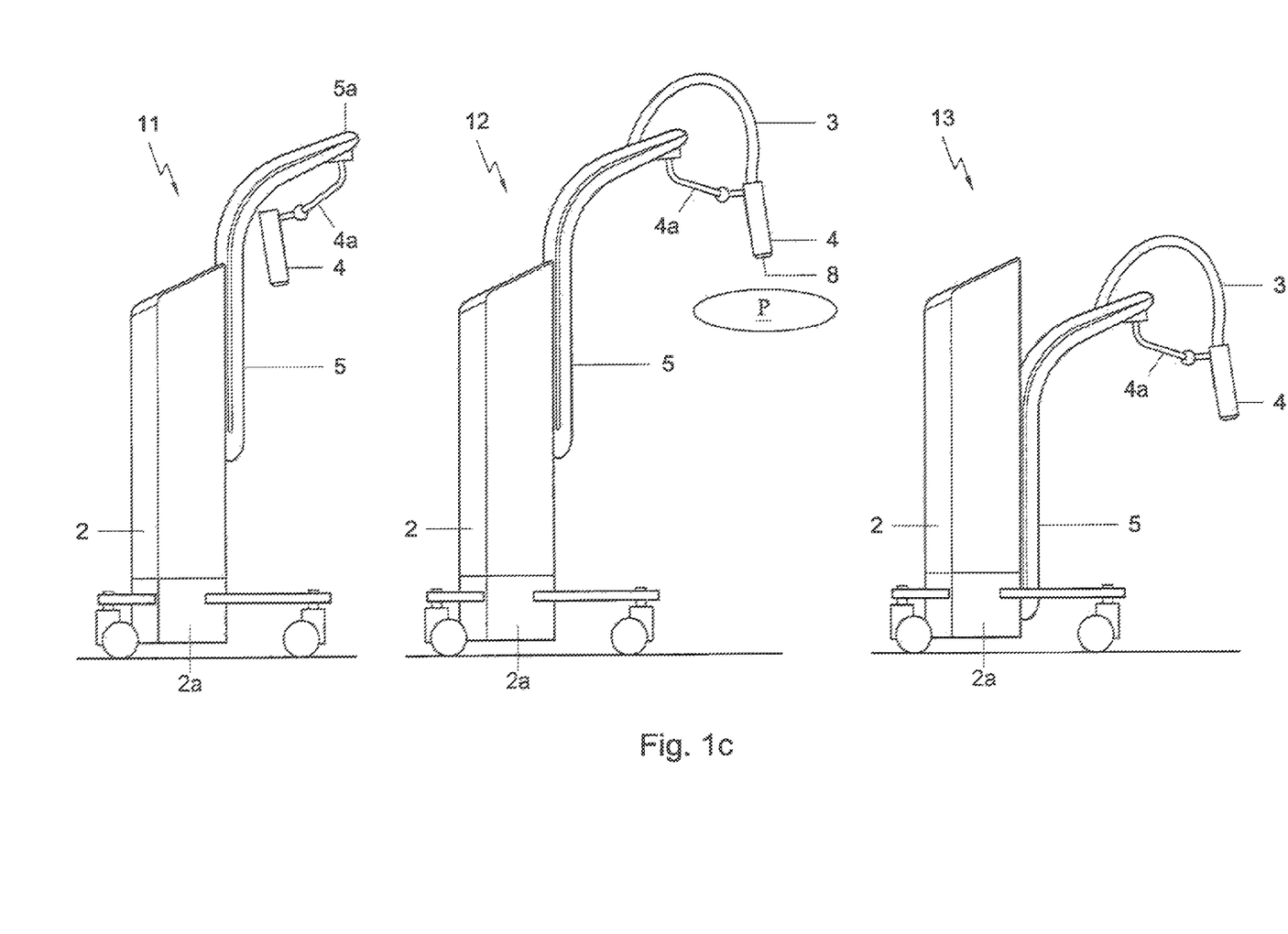
FIG. 1c presents a schematic view of the X-ray unit shown in FIGS. 1a and 1b, illustrating displacement of an X-ray applicator of the X-ray unit relative to a base of the X-ray unit, according to embodiments of the present disclosure.

FIG. 1c illustrates the displacement of the X-ray applicator 4 of the X-ray unit 10. In accordance with an aspect of the present disclosure, mobile X-ray unit 10 may be configured so as to support a broad range of translational and rotational movements of the X-ray applicator 4.

In view 11, the X-ray applicator 4 is in a retracted position. It will be appreciated that cabling is not depicted for clarity reasons. The retracted position may be suitable for transport of the mobile X-ray unit 10 towards a booth and/or for maneuvering the X-ray unit 10 around the patient. In order to retract the X-ray applicator 4 as close as possible to the base 2, the articulated arm 4a may be positioned under the outer portion 5a of the displaceable panel 5. For ensuring stability of the mobile X-ray unit 10 during maneuvering thereof, a load block 2a may be provided for lowering the point of gravity of the X-ray unit 10.

In view 12, the X-ray applicator 4 may be in an extended position having an X-ray exit surface 8 oriented towards a patient P. In order to suitably position the X-ray applicator 4 with respect to the patient P, the displaceable panel 5 may be moved to an intermediate position located between a lowest stand position and a highest stand position of the displaceable panel 5. The articulated arm 4a may be used for suitably rotating the X-ray applicator 4 about a rotation axis. Preferably, a rotation axis is selected to coincide with a direction of emanation of the X-ray beam from the exit surface 8 for a vertically oriented X-ray applicator 4.

In view 13, the X-ray applicator 4 may be in a lowered stand position. For this purpose the displaceable panel 5 may be in its lowest position and the arm 4a may be used for orienting the X-ray applicator 4 in a desirable way.

Figure 2:
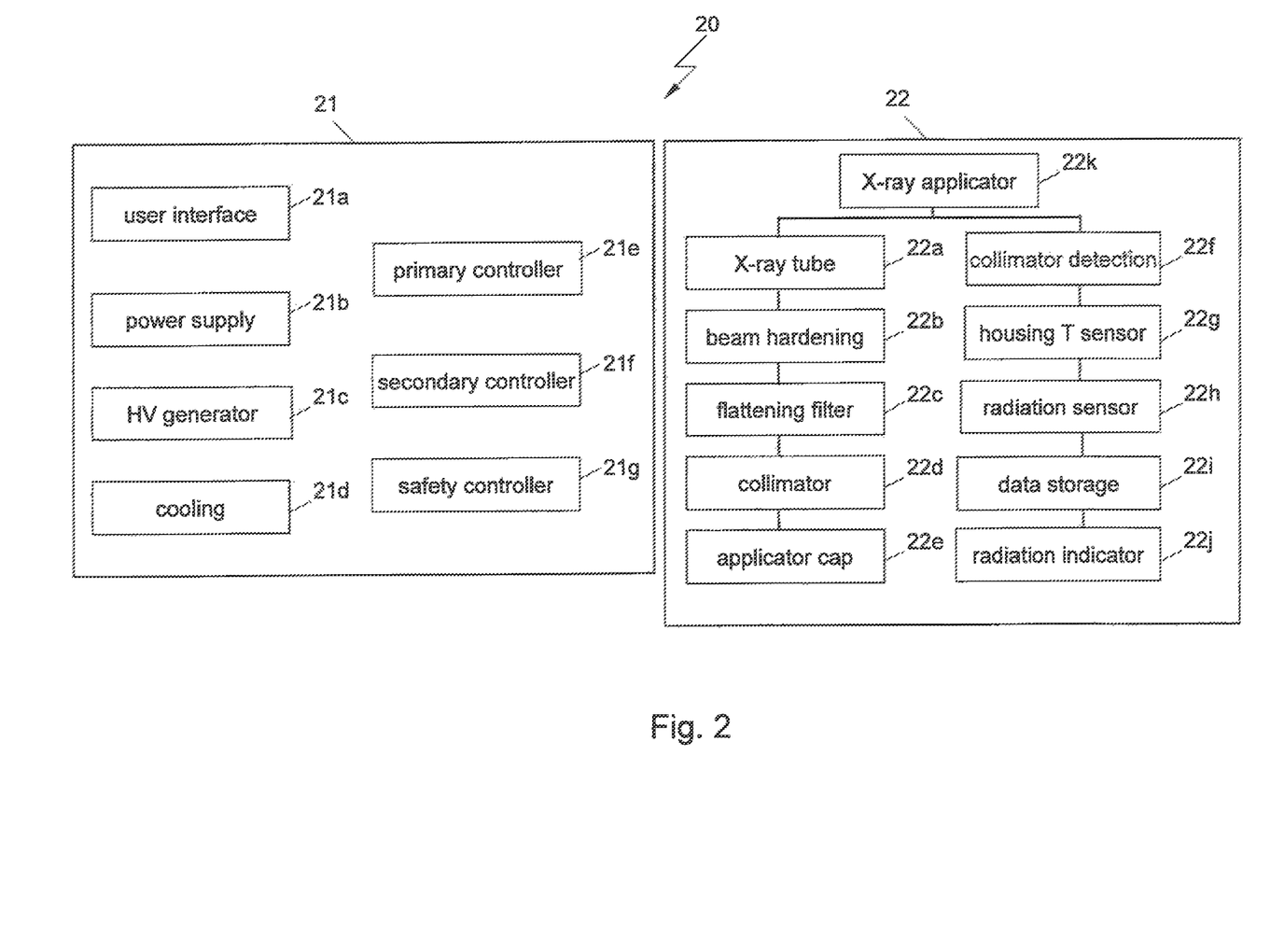
FIG. 2 presents a diagrammatic representation of the mobile X-ray unit, according to embodiments of the present disclosure.

FIG. 2 is a diagrammatic representation of the mobile X-ray unit 10. The mobile X-ray unit 10 may include a high voltage supply, preferably adapted to generate 50-75 kV X-rays in a suitable X-ray tube 22a, a cooling system 21d for cooling the X-ray tube during use, and a control system 21 for controlling electronic and electric parameters of sub-units of the X-ray unit during use. View 20 diagrammatically depicts main units of the control system 21 and of the X-ray applicator 22.

The control system 21 includes a hard wired user interface 21a for enabling switching on and switching off of the high voltage supply 21b. In some embodiments, the high voltage supply 21b comprises a high voltage generator 21c with improved ramp-up and ramp-down characteristics. The high voltage supply is preferably operable for delivering power of about 200 W in use. In some embodiments, the ramp-up time may be of the order of 100 ms. The hard wired interface 21a, may also be arranged to automatically switch on the cooling system 21d when the high voltage generator is switched on. In addition, the control system 21 may include a primary controller 21e arranged for controlling the dose delivery from the X-ray applicator 22 in use. The primary controller 21e may be provided with a primary counter adapted to register time lapsed after the X-ray radiation is initiated. The primary counter may then automatically switch off the high voltage supply to the X-ray tube 22a in the event a pre-determined dose is reached. It will be appreciated that the pre-determined dose is at least dependent on the energy of the X-rays and the dose rate, which may be calibrated in advance. Where calibrated data is made available to the primary controller, adequate primary dose delivery control may be achieved. In some embodiments, a secondary controller 21f may be provided for enabling an independent loop of dose delivery control. The secondary controller 21f may be connected to a dose meter accommodated inside the X-ray applicator 22 in the X-ray field before the collimator 22d. Accordingly, the dose meter may provide real-time data on actual dose delivery taking into account dose variation during ramp up and ramp down of the high voltage source. Still preferably, the control system 21 may include a safety controller 21g adapted to compare readings from the primary controller 21e and the secondary controller 21g for switching off the high voltage generator 21c after a desired dose is delivered. Additionally and/or alternatively, the safety controller 21g may be wired to guard emergency stop, door interlock, and a generator interlock.

In an exemplary embodiment, the X-ray applicator 22 may include an X-ray tube 22a housed in an outer housing (shielding) 22k. The X-ray tube 22a may have a target-collimator distance between 4 and 10 cm, and preferably between 5 and 6 cm. The X-ray applicator 22 may further include a beam hardening filter 22b selected to intercept low-energy radiation and a beam flattening filter 22c, designed to intercept portions of X-ray radiation for generating a substantially flat beam profile near the exit surface of the X-ray applicator 22. Further, the X-ray applicator 22 may comprise one or more collimators 22d arranged to define treatment beam geometry. Preferably a set of collimators 22d may be used having, for example, diameters of 1, 1.5, 2, 2.5, 3, 3.5, 4, 4.5, and 5 cm. It will be appreciated that although circular collimators are discussed, collimators of any shape, such as square, elliptic, or custom made collimators are possible. It may be advantageous to have an X-ray applicator 22 with automatic collimator detection device 22f adapted to automatically signal which collimator is being used. In some embodiments, resistive sensing may be used to identify which collimater 22d is being used. In particular, each collimator 22d may be provided with at least a couple of projections for bridging a resistive path of a collimator receptacle. The resulting electrical resistance of the receptacle constitutes a signal indicating that a collimator 22d is being used.

The X-ray applicator 22 may also include a built-in temperature sensor 22g adapted to signal temperature of the X-ray tube 22a and/or its shielding 22k. The signal from the temperature sensor 22g may be received by the control system 21 which may carry out the analysis thereof. Should the measured temperature be elevated beyond an allowable level, an alarm signal may be generated. Optionally, a shut-off signal to the high voltage generator may be provided. The X-ray applicator 22 may further comprises a radiation sensor 22h arranged inside the outer housing 22k for detecting X-ray radiation which may be delivered by the X-ray tube 22a. Preferably, for safety reasons the X-ray applicator 22 may include a non-volatile data storage 22i arranged for recording operational parameters at least of the X-ray tube 22a. Further, to enhance radiation safety, the X-ray applicator 22 may be provided with a radiation indicator 22j arranged for providing a visual and/or an audio output to the user and/or the patient regarding ON/OFF condition of the X-ray tube 22a. It will be appreciated that the radiation indicator 22j may comprise a plurality of signaling devices. In one embodiment, at least one signaling device, for example a light emitting diode (LED), is associated with the X-ray applicator 22 and provided on the X-ray applicator 22. It is understood, however, that the signaling devices may be positioned at any other location on the mobile X-ray unit.

FIG. 3 presents a cross-section of an X-ray applicator of the mobile X-ray unit. The X-ray applicator 30 include an outer housing 36 accommodating the X-ray tube assembly 35 provided with external shielding 35a. In use, the X-ray applicator 30 may be maneuvered by the user by holding the housing 32. The X-ray applicator 30 includes a target element 45 of an anode arranged to emit a beam of X-rays and having a longitudinal propagation axis 45a. The target element 45 may be disposed on an outer surface of anode and perpendicular to a longitudinal axis of the anode. In accordance to one aspect of the present disclosure, the distance between the target element and the collimator 33 may be in the range between 4 and 10 cm, and preferably between 5 and 6 cm. Such a relatively short target-collimator distance may generate an X-ray beam having a substantially narrow penumbra (1.5-1.8 mm for 20/80% lines) and good beam flatness. The X-ray applicator 30 further includes a filter 39 for hardening the X-ray beam emanating from the target 45, a beam flattening filter 40 for flattening out a beam profile, and collimator 33 insertable in a collimator receptacle 41.

A cooling system 34 may be provided so as to prevent overheating of the X-ray tube 35. In one embodiment, the cooling system 34 may be arranged in the space between the X-ray tube 35 and the shielding 35a in contact with the surface of the X-ray tube 35. A suitable coolant may be provided using a pipe 31. It is contemplated that the coolant may be water, a pressurized gas, or even a special oil. The X-ray applicator 30 may further comprise a temperature sensor 37.

The X-ray assembly 30 may further include a suitable radiation detector 38, connected to a radiation indicator 43. Data collected by the radiation detector 38 may be stored in a data storage unit 44.

In order to protect an X-ray exit surface of the X-ray applicator 30 from intra-patient contamination, an applicator cap 42 may be provided to cover at least the exit surface of the X-ray applicator 30. Preferably, the applicator cap is thick enough to fully intercept secondary electrons emanating from the X-ray applicator 30.

Figure 4:
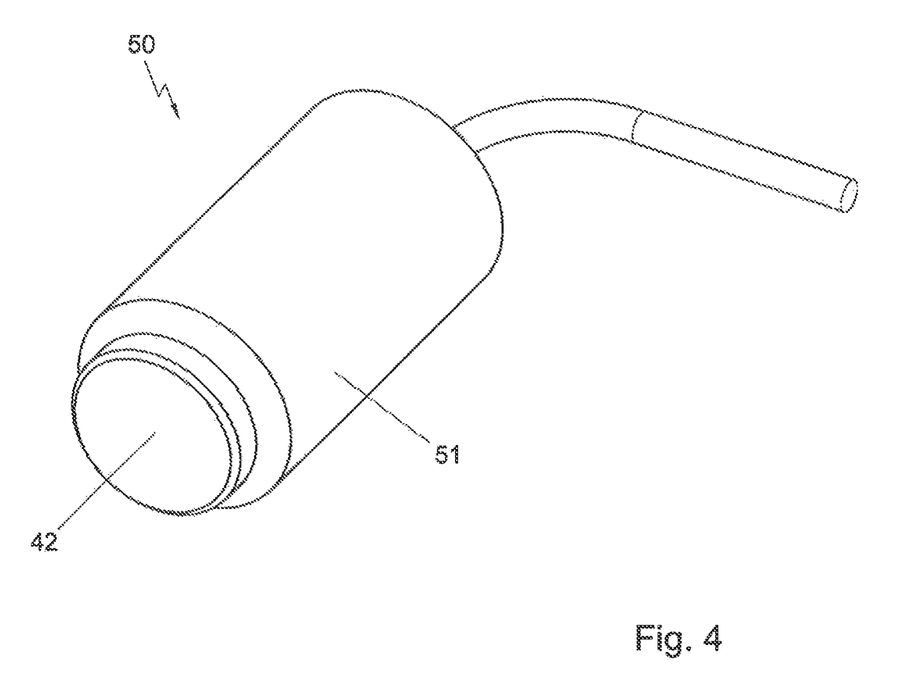
FIG. 4 presents a partial perspective view of the X-ray applicator of FIG. 3 provided with an applicator cap, according to embodiments of the present disclosure.

FIG. 4 presents a partial perspective view of X-ray applicator 30 of FIG. 3 provided with an applicator cap 42. The applicator cap 42 may be manufactured from a material that is transparent to X-rays, such as glass, plastics, or ceramics materials. Particularly, when the X-ray applicator 30 comprises a light source conceived to at least partially delineate the X-ray field, a material of the applicator cap 42 has at least 50% transparency of a wavelength of light emitted by the light source.

In some embodiments, the applicator cap 42 may be manufactured from PVDF and may have a thickness of about 0.4-0.7 mm, and preferably 0.6 mm, across the window portion. The applicator cap 42 may have density of about 1.75-1.8, and preferably 1.78. Alternatively, the applicator cap 42 may have a thickness of 0.3-0.6 mm, and preferably 0.5 mm, across the window portion. In this embodiment, the applicator cap may have a density of 1.30-1.45, and preferably 1.39, and may be manufactured from PPSU. It is found that these materials may be particularly suitable as they as stable under influence of the X-rays and are suitable for different types of sterilization procedures, such as chemical sterilization, or sterilization under elevated temperatures.

Applicator cap 42 may also be manufactured from a metal. In this embodiment, the applicator cap may be sterilized, otherwise, the applicator cap 42 may be a disposable applicator cap. In view 50 of FIG. 4, it is seen that the outer dimension of the X-ray applicator 51 may be larger than the outer dimension of the exit portion covered by the applicator cap 42. Although such embodiment is preferable for minimizing total weight of the X-ray applicator 51, it is possible that the exit portion has the same dimension as the body of the X-ray applicator 51.

Figure 5:
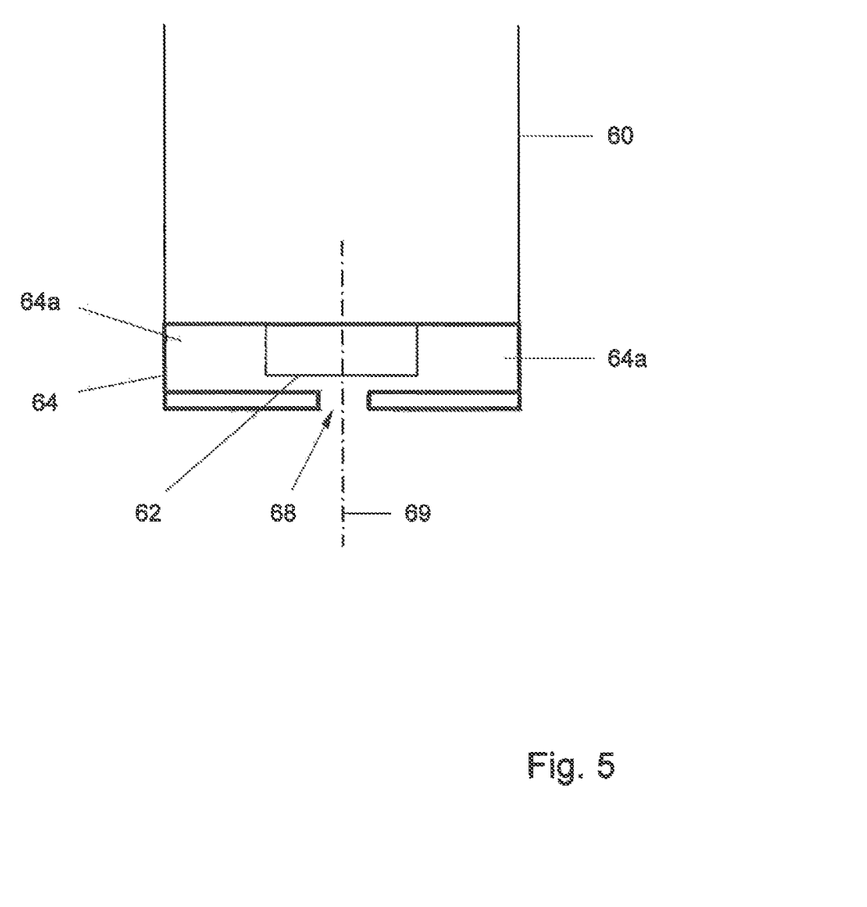
FIG. 5 presents a schematic top view of the X-ray applicator provided with the applicator cap, according to embodiments of the present disclosure.

FIG. 5 presents a schematic view of another embodiment of the applicator cap. In this embodiment, the X-ray applicator 60 includes an exit surface 62 and an applicator cap 64. The applicator cap 64 may be an exchangeable, preferably disposable, applicator cap 64. In accordance with this embodiment, the cap 64 may be attached to the X-ray applicator 60 in a plurality of ways. For example, applicator cap 64 may be releasably attached to X-ray applicator 60 using a Velcro mechanism. Alternatively, the cap 64 may be provided with a fixing agent, such as, for example, a self gluing tape or any other known fixing agent. Still alternatively, the cap 64 may be provided with projections or cavities arranged to cooperate with respective cavities or projections disposed on the X-ray applicator 60 for fixing the applicator cap 64 to the X-ray applicator 60.

The cap 64 may extend proximally of the exit surface 62 of the X-ray applicator 60 so as to surround a distal portion of the X-ray applicator 60 and form a concentric cavity 64a. It will be appreciated that it is possible to provide the cap with one or more compartments for utility purposes in the area not interfering with the exit surface. For example, the lateral area 64a may be used to accommodate a light source 66, such as, for example a LED, and a portable source, such as, for example, a battery. The central portion of the cap 64 may be provided with a small opening 68 for allowing light generated by the light source to propagate along the central axis 69 of the X-ray applicator 60. In this way, the cap 64 may be provided with alignment mechanism facilitating proper alignment of the X-ray applicator 60 prior to use.

Alternatively, the cap 64 may be provided with a transparent region through which the light may pass. This may advantageously maintain complete cover over the exit surface 62 of the X-ray applicator.

Figure 6:
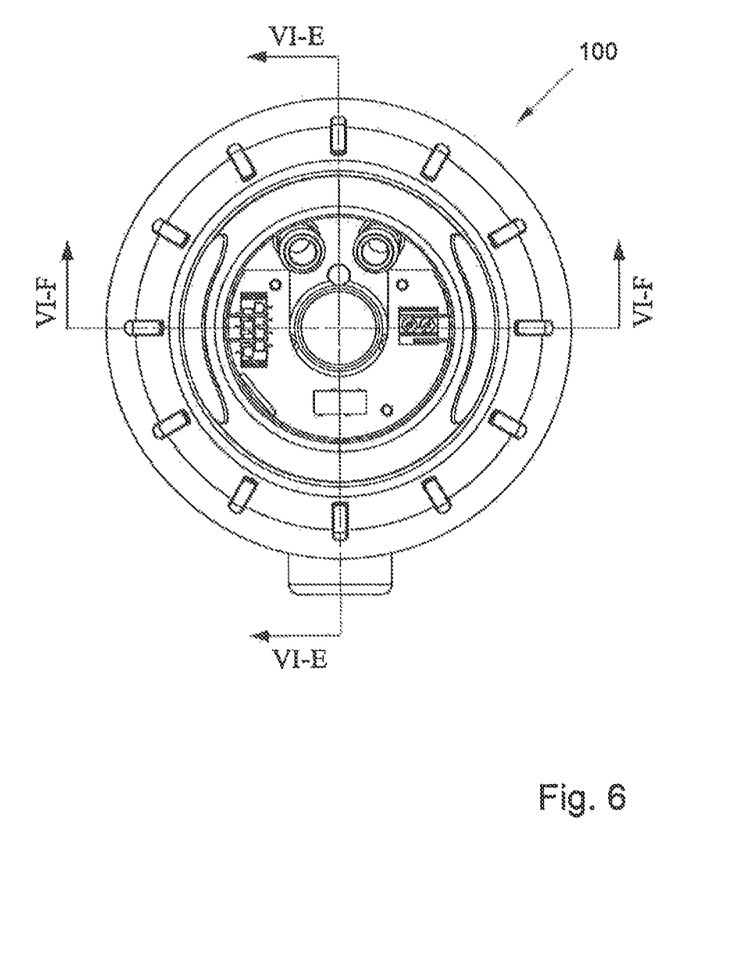
FIG. 6 presents an end view of an X-ray tube, according to embodiments of the present disclosure.

FIGS. 6, 6E-E, and 6F-F, illustrate various views of the X-ray tube. The X-ray tube 100 has a body 102 enclosing at one end an end window 104 through which the X-rays pass, see FIG. 6 cross-section E-E. The end window 104 is made from a thin sheet of Beryllium metal. An applicator cap 106 may be positioned over the end window 104 so as to covering the end window 104 and protect end window 104. Applicator cap 106 may be made from a plastic material. The applicator cap may be manufactured from PVDF (polyvinylidene fluoride) and has a thickness of about 0.4-0.7 mm, and preferably 0.6 mm, across the window portion, as described in more detail above. Alternatively, the applicator cap 106 may be manufactured from PPSU (polyphenylsulfone) and have a thickness of about 0.3-0.6 mm, and preferably 0.5 mm, across the window portion, also as described above in more detail.

In the tube body 102 a target element 108 is located at a range between 4 and 10 cm from the collimator 130, and preferably between 5 and 6 cm from the collimator 130 (see FIG. 6, cross-section F-F). It will be appreciated that this distance is measured between the outer surface of the target element 108 and a midplane of the collimator 130. The target 108 may be made from Tungsten metal to provide the desired X-ray spectrum. The tungsten tip of the target element 108 may be mounted on a large anode assembly 110 which also serves to conduct away the heat created from the generation of the X-rays in the target 108. Most of the anode assembly 110 is made from copper. The cathode 112 (see FIG. 6, cross-section F-F) may be located slightly off-axis near the end window 104. Electrons emitted from the cathode are accelerated across the gap by the potential difference between the cathode and anode, in this case set at about 70 kV, to the target 108 where the impact causes the generation of X-rays in a known manner. X-rays emitted from the target element 108 pass through a beam hardening filter 122 before passing through a collimator 130 and an exit surface 124 on an applicator cap 106. The collimator 130 may be housed in a suitable collimator receptacle 128.

The anode assembly 110 may be mounted in the body 102 and electrically insulated. One of a number of known techniques and materials can be used to provide the desired level of insulation between the anode assembly 110 and the body 102.

As is well known in the art, the production of X-rays generates large amounts of waste heat. Accordingly, it may be necessary to cool the X-ray tube 100 in order to maintain it at a safe temperature. Various cooling mechanisms are known and used in the art. In one embodiment, the X-ray tube 100 is cooled by cooled water forced around the anode region. Cooled water enters the back of the tube by a first conduit 116 and leaves by a second conduit 118 (see FIG. 6, cross-section F-F). The water cooling circuit is a closed loop circuit, with the water leaving the tube assembly 105 to be cooled by a remote cooler (not shown) before returning to the X-ray tube 100. It is contemplated that oil or another liquid may be used as the cooling medium. It is also known that a pressurized gas may be used as an effective coolant in some applications.

As is known in the art, X-rays are generated and emitted in all directions, however the body 102 of the X-ray tube 100 and other internal components will tend to reduce the amount of radiation emitted from the body 102 of the X-ray tube 100 to a minimum, with most of the radiation emitted from the end window 104. The thickness of the shielding provided by the body 102 may be designed so that it provides at least the minimum level of shielding required for safe use by the operator.

A high voltage cable assembly 120 is connected to the anode assembly 110. The high voltage cable assembly 120 may be connected to flexible cable means (not shown) which in turn may be connected to a high voltage power supply.

A radiation detector 114 may be placed outside the path of the X-ray beam emitted from the target 108 and passing through the end window 104. This detector can be any known form of radiation detector. In one embodiment, the radiation detector may be a hardened semi-conductor connected to an amplifier. The radiation detector 114 may detect when the tube 102 is working and emitting X-ray energy. Output from the detector 114 may connected to a control unit, and the output signals from the detector 114 may be used to provide an optical indication to a user of whether the tube is operating or not. By this means an X-ray detector 114 may be provided which may be used to detect if the X-ray tube is on or off.

With further calibration of the radiation detector 114, it may be possible to determine and calculate the X-ray dose administered to the patient during the treatment. Thus, it may be possible to have a real time dosimetry measurement system, in which the precise amount of radiation dose administered can be determined. Once the dose rate is known, a treatment plan can be modified during treatment. This is advantageous because it enables a very accurate and carefully controlled dose of X-rays to be administered.

In order to enable the X-ray tube 100 to be placed accurately over a tumour, a tumour illumination device may be is used. The tumour illumination device may include a plurality of lights 126 placed around the circumference of the X-ray tube 100 near the end window 104. When in use, the lights shine onto the skin of the patient. Since the lights 126 are positioned around the circumference of the tube body 102, at a short distance from the end of the X-ray tube 100 they create a circle of light with a sharp cut off of the inner part of the circle. In this way, the position of the lights on the tube body 102 may create a shadow. This shadow circle may be used to indicate the region which will be subject to irradiation when the X-ray tube 100 is turned on. It should be appreciated the area within the circle may not be completely dark; and that the ambient light may be able to enter the shadow region.

In some embodiments, the lights 126 are white LEDs which can be bright enough to clearly illuminate the target region but do not generate a large amount of heat. The lack of heat generation is important because the lights will be in close proximity to the skin of the patient, and so it is important to minimize the risk of burning and/or damaging the skin. Other colours of LEDs may be used. Alternatively, other light sources may be used, such as known filament lamps or even a remote light source connected to the ring by fiber optic cables.

It will be appreciated that the illumination devices 126 are particularly advantageous when the X-ray applicator discussed above is provided with the applicator cap, as light emanating from the inside the X-ray tube 102 may be too diffuse when exiting the applicator cap.

It is found to be sufficient to use the shadow of the X-ray applicator, as generated by the lateral illumination device 126, as in the field of the radiotherapy substantial margins, such as 0.5-1 cm around a target area, are used. It may also possible to calibrate the distance between the central axis of the X-ray applicator and the beam delivered by the illumination device 126. In this way, the X-ray applicator may be first positioned with the beam at a center of the target region and then translated along a known distance.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

What is claimed is:

1. A device for radiation therapy, the device comprising:
   an X-ray applicator for emitting an X-ray beam along a longitudinal axis through an exit portion of the X-ray applicator;
   an applicator cap for at least partially covering the exit portion of the X-ray applicator; and
   a light source for delineating at least a portion of the X-ray beam emitted by the X-ray applicator;
   wherein at least a cover region of the applicator cap through which the X-ray beam propagates is transparent to a wavelength of light generated by the light source.

2. The X-ray device according to claim 1, wherein the applicator cap is manufactured from glass, plastic, ceramic, or metal materials.

3. The X-ray unit according to claim 1, wherein the applicator cap includes a body that extends both proximally and distally with respect to the exit surface.

4. The X-ray device according to claim 3, wherein a thickness of the body is sufficient to substantially eliminate electron contamination from the X-ray beam.

5. The X-ray device according to claim 1, wherein the cover region of the applicator cap is at least 50% transparent for a wavelength of light generated by the light source.

6. The X-ray device according to claim 3, wherein the body defines a cavity extending from the proximal end of the body to the distal end of the body and the light source is disposed in the cavity.

7. The X-ray unit according to claim 1, wherein the light source includes a plurality of lights positioned around the X-ray applicator, such that the light output by the plurality of lights delineate at least a portion of the X-ray beam.

8. The X-ray unit according to claim 3, wherein the light source and the body are positioned such that the light source is configured to generate a shadow corresponding to a region of the X-ray beam.

9. The X-ray unit according to claim 1, wherein the X-ray beam is used to treat an treatment area of a patient, and wherein the transparent portion of the applicator cap is configured to allow visible delineation of the treatment area.

10. The X-ray unit according to claim 1, wherein the light source is a first light source and the X-ray unit further includes a second light source positioned in an X-ray tube of the X-ray applicator and offset from the longitudinal axis for illuminating at least a portion of a target region of the X-ray beam emitted by the X-ray applicator.

11. The X-ray unit according to claim 1, wherein a cover region of the applicator cap through which the X-ray beam propagates is substantially flat.

12. The X-ray unit according to claim 11, wherein the applicator cap is provided with at least one connector for coupling the applicator cap to the X-ray applicator.

13. The X-ray unit according to claim 1, wherein the X-ray applicator includes an X-ray tube, and the X-ray tube includes a target element for generating an X-ray beam and a collimator for shaping the generated X-ray beam.

14. The X-ray unit according to claim 13, wherein the distance between the target element and the collimator is between 4 and 10 cm.

15. The X-ray unit according to claim 13, wherein a direction of propagation of the X-ray beam is substantially parallel to a longitudinal axis of the X-ray tube.

16. The X-ray unit according to claim 13, wherein the target element is provided on an anode that is disposed substantially coaxially with a longitudinal axis of the X-ray tube.

17. The X-ray unit according to claim 1, wherein the applicator cap is configured to intercept secondary electrons emanating from the X-ray applicator.

* * * * *